(12) United States Patent
Nishiuma et al.

(10) Patent No.: US 7,692,791 B2
(45) Date of Patent: Apr. 6, 2010

(54) TARGET SUBSTANCE-DETECTING APPARATUS AND TARGET SUBSTANCE-DETECTING METHOD

(75) Inventors: Satoru Nishiuma, Kawasaki (JP); Norihiko Utsunomiya, Machida (JP); Tetsunori Ojima, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 144 days.

(21) Appl. No.: 12/143,604

(22) Filed: Jun. 20, 2008

(65) Prior Publication Data

US 2008/0316486 A1    Dec. 25, 2008

(30) Foreign Application Priority Data

Jun. 21, 2007    (JP)    ............................... 2007-163712

(51) Int. Cl.
*G01J 4/00*    (2006.01)
(52) U.S. Cl. ...................... 356/364; 250/225; 356/435
(58) Field of Classification Search ......... 356/364–369, 356/432, 435; 250/225
See application file for complete search history.

(56) References Cited

U.S. PATENT DOCUMENTS

| | | | |
|---|---|---|---|
| 6,180,415 B1 | 1/2001 | Schultz et al. | |
| 7,233,396 B1* | 6/2007 | Hall et al. | ................... 356/369 |
| 7,286,221 B2* | 10/2007 | Caracci et al. | ............... 356/300 |
| 7,384,561 B2 | 6/2008 | Utsunomiya | |
| 7,387,901 B2 | 6/2008 | Nishiuma et al. | |
| 7,403,287 B2 | 7/2008 | Ogawa et al. | |
| 2006/0170918 A1 | 8/2006 | Nishiuma | |
| 2007/0105087 A1 | 5/2007 | Ban et al. | |
| 2007/0248987 A1 | 10/2007 | Imamura et al. | |
| 2007/0248991 A1 | 10/2007 | Ojima et al. | |
| 2007/0285666 A1 | 12/2007 | Utsunomiya et al. | |

FOREIGN PATENT DOCUMENTS

JP    2001513198    8/2001

(Continued)

OTHER PUBLICATIONS

U.S. Appl. No. 12/088,023, International Filing Date: Dec. 20, 2006, Yamamichi, et al.

(Continued)

*Primary Examiner*—L. G Lauchman
(74) *Attorney, Agent, or Firm*—Fitzpatrick, Cella, Harper & Scinto

(57) ABSTRACT

A target substance-detecting apparatus comprises a target substance-detecting element comprising metal structures, a light irradiation section for irradiating the target substance-detecting element with a light, a light-polarizing section which polarizes the irradiating light and separates an output light emitted from the target substance-detecting element into a first polarized light and a second polarized light, first and second light-receiving sections for outputting first and second signals according to intensity of the first and second polarized lights, respectively; and a control section which determines peaks of absorbances of the first and second polarized lights by measuring the absorbances from the first and second signals respectively, and controls the target substance-detecting element so that the peak values of the first and second absorbances can be maximized and minimized respectively by controlling a incidence angle of formed by a vibration direction of the incident light and a main axis of the target substance-detecting element.

9 Claims, 14 Drawing Sheets

FOREIGN PATENT DOCUMENTS

JP        2005156414        6/2005

OTHER PUBLICATIONS

U.S. Appl. No. 10/582,805, International Filing Date: Apr. 27, 2006, Yamamichi, et al.

U.S. Appl. No. 12/159,391, International Filing Date: Jan. 17, 2007, Nishiuma, et al.

U.S. Appl. No. 11/688,066, filed Mar. 14, 2007, Utsunomiya, N.

* cited by examiner 1402   1401

TARGET SUBSTANCE-DETECTING APPARATUS AND TARGET SUBSTANCE-DETECTING METHOD

BACKGROUND OF THE INVENTION

1. Field of the Invention

The present invention relates to a target substance-detecting apparatus for detecting a target substance by using a plasmon resonance phenomenon of a metal, and a target substance-detecting method therefor.

2. Description of the Related Art

There are a plurality of disease markers for particular diseases such as malignant tumor, hepatitis, diabetes mellitus and osteoporosis, in blood, and when a person is afflicted with a disease, the concentration of a particular protein changes (increase or decrease) compared to a usual condition. For this reason, it leads to an early detection of serious diseases to monitor the disease markers in normal times, which is expected as the next generation of a medical technology.

In addition, it is thought that the transition and recurrence of a tumor can be early detected by monitoring a tumor marker relating to the malignant tumor after the tumor has been removed, and the monitoring is expected to largely contribute to the improvement of medical quality.

In recent years, Food Sanitation Law has been revised, and business undertakers are required to display egg, peanut, buckwheat, wheat and milk on their products when they are contained in a food. However, there are few people who know, quantitatively, how much allergic predisposition they have and to which kind of foods. Accordingly, it is important to scientifically know these data as a numeric value, from the viewpoint of health promotion and preventive medical practice for each person.

A method of analyzing a raw and unpurified protein occasionally employs a sensor which identifies a particular compound by using a biological ligand-analyte interaction.

There are several types of sensors which employ several detection methods such as a fluorescent immunoassay technique, a plasmon resonance technique and a light interference technique. Any type of the techniques commonly has the steps of immobilizing a ligand on the surface of the sensor, and making the ligand bonded to an analyte in a specimen with high sensibility and high selectivity to remove concomitants and to catch only an objective analyte (target substance) with high efficiency.

The plasmon resonance technique measures the concentration of the target substance specifically bonded to the ligand immobilized on a metallic thin film or fine particles of a metal, by using a phenomenon that a metal responds to a change of an optical refractive index of an interface material with high sensibility. The above ligand is immobilized on the surface of the sensor by using a chemical or a physical technique.

The plasmon resonance technique can obtain information on the change (kinetics) with time of a reaction between the ligand and the analyte, which is thought to be an advantage in addition to a feature of needing no labeling.

As for an apparatus using the plasmon resonance, various techniques are proposed in order to improve a detection performance for the target substance. The techniques are disclosed, for instance, in Japanese Patent Application Laid-Open No. 2005-156414 and Japanese Patent Application Laid-Open No. 2001-513198.

An apparatus which is disclosed in Japanese Patent Application Laid-Open No. 2005-156414 is an apparatus which polarizes an incident light into a P wave and an S wave, then irradiates the sensor with the lights of the waves, makes a photodetector measure the intensity of reflected light based on a signal from the P wave, and sense the intensity of a light source or the change of sensibility of the photodetector based on a signal from the S wave. Thereby, the apparatus can accurately detect the target substance even when the intensity of the light source or the sensibility of the photodetector has changed.

An apparatus which is disclosed in Japanese Patent Application Laid-Open No. 2001-513198 is an apparatus which intends to improve its detection sensibility for the target substance, and which detects light scattered by metal microparticles with the photodetector while using a dark field optical system suitable for detecting the microparticles, and analyzes the detection contents of the photodetector with an image processor to specify the target substance.

When a target substance is detected by using plasmon resonance, and when metal structure have a rectangular shape, for instance, and have anisotropy in a plane perpendicular to an incident light, the target substance-detecting element greatly varies its optical characteristics depending on a direction in which the target substance-detecting element has been irradiated with the incident light. Thereby, a plasmon resonant state does not significantly appear, and the apparatus may lower its detection accuracy for the target substance.

Even the apparatuses disclosed in Japanese Patent Application Laid-Open No. 2005-156414 and Japanese Patent Application Laid-Open No. 2001-513198 are not provided with a device considering the shape of the target substance-detecting element, when the target substance-detecting element is irradiated with an incident light, and accordingly are thought to occasionally cause the above described problem.

The present invention has been designed so as to solve the above described problem, and is directed at providing a target substance-detecting apparatus for detecting a target substance with high accuracy and a target substance-detecting method therefor.

SUMMARY OF THE INVENTION

The present invention is directed to a target substance-detecting apparatus comprising: a target substance-detecting element comprising metal structures; a light irradiation section for irradiating the target substance-detecting element with a light; a light-polarizing section which polarize an input light and separates an output light emitted from the target substance-detecting element into a first polarized light and a second polarized light having a vibration direction different from that of the first polarized light; a first light-receiving section for outputting a first signal according to intensity of the first polarized light; a second light-receiving section for outputting a second signal according to intensity of the second polarized light; and a control section which determines a peak of absorbance of the first polarized light by measuring the absorbance from the first signal, determines a peak of absorbance of the second polarized light by measuring the absorbance of the second polarized light from the second signal, and controls the target substance-detecting element so that the peak value of the first absorbance can be maximized and simultaneously the peak value of the second absorbance can be minimized by controlling an incident angle of formed by a vibration direction of the incident light and a main axis of the target substance-detecting element.

The target substance-detecting apparatus can further comprise: a data processing section having a memory device, wherein the memory device has standard data of the first absorbance based on the intensity of the first polarized light and the second absorbance based on the intensity of the second polarized light, according to each of the angles of incidence of lights.

The control section can have a rotation mechanism which varies the peak values of the first absorbance and the second absorbance by rotating the target substance-detecting element or a vibration direction of the incident light, and determines an angle to which the rotation mechanism rotates the target substance-detecting apparatus, based on a plurality of the standard data stored in the memory device.

The present invention is directed to a method for detecting a target substance comprising the steps of: irradiating a target substance-detecting element comprising metal structures with the polarized light; separating a light emitted from the target substance-detecting element into a first polarized light and a second polarized light having a vibration direction different from that of the first polarized light; determining a peak of first absorbance by measuring the first absorbance based on intensity of the first polarized light; determining a peak of second absorbance by measuring the second absorbance based on intensity of the second polarized light; maximizing the peak value of the first absorbance and simultaneously minimizing the peak value of the second absorbance based on each of the peak values by controlling an incidence angle formed by a vibration direction of the incident light and a main axis of the target substance-detecting element; and detecting the target substance.

The method of maximizing the peak value of the first absorbance and simultaneously minimizing the peak value of the second absorbance based on each of the peak values can be a method of determining an angle of incidence of the light, which maximizes the peak value of the first absorbance and simultaneously minimizes the peak value of the second absorbance and rotating the target substance-detecting element so as to form the angle of incidence.

The method of maximizing the peak value of the first absorbance and simultaneously minimizing the peak value of the second absorbance based on each of the peak values can be a method of rotating a vibration direction of the incident light.

The method of maximizing the peak value of the first absorbance and simultaneously minimizing the peak value of the second absorbance based on each of the peak values can be a method of: comparing the peak value of the first absorbance and the peak value of the second absorbance with standard data including the first absorbance based on the intensity of the first polarized light and the second absorbance based on the intensity of the second polarized light, according to each of the angles of incidence of the light incident on the target substance-detecting element, which have been previously obtained; determining an angle of incidence of the light incident on the target substance-detecting element; and rotating the target substance-detecting element or a vibration direction of the incident light.

The method of maximizing the peak value of the first absorbance and simultaneously minimizing the peak value of the second absorbance based on each of the peak values can be a method of: comparing the peak value of the first absorbance and the peak value of the second absorbance with standard data including the first absorbance based on the intensity of the first polarized light and the second absorbance based on the intensity of the second polarized light, according to each of the angles of incidence, which have been previously obtained; calculating a correction factor C from the peak value of the first absorbance for a light with the angle of incidence in the standard data and the maximum peak value of the first absorbance in the standard data; and correcting a measured value with the use of the correction factor C.

The present invention is directed to a target substance-detecting apparatus comprising: a target substance-detecting element absorbance of which varies according to a wavelength of an incident light; a light irradiation section for irradiating the target substance-detecting element with a linearly polarized light which is the incident light, while changing the wavelength of the incident light; a polarizing section that separates a transmitted light when the target substance-detecting element has been irradiated with the incident light into a first polarized light and a second polarized light having a vibration direction different from that of the first polarized light; a first light-receiving section for outputting a first signal according to intensity of the first polarized light, and a second light-receiving section for outputting a second signal according to intensity of the second polarized light; and a control section which determines a peak of first absorbance by measuring the first absorbance from the first signal, determines a peak of second absorbance by measuring the second absorbance from the second signal, and controls the target substance-detecting element so that the peak value of the first absorbance can be maximized and the peak value of the second absorbance can be minimized based on the respective peak values.

The control section can have a rotation mechanism which varies the peak values of the first absorbance and the second absorbance by rotating the target substance-detecting element. The control section can make the rotation mechanism rotate the target substance-detecting element until the peak value of the second absorbance becomes smaller than a predetermined threshold value. The target substance-detecting apparatus can further comprise a memory device for storing a plurality of standard data including the first absorbance based on the intensity of the first polarized light and the second absorbance based on the intensity of the second polarized light, which correspond to a plurality of rotation angles of the target substance-detecting element respectively, according to each of the rotation angles, wherein the control section determines the angle to which the rotation mechanism rotates the target substance-detecting element with the use of the plurality of the standard data stored in the memory device.

The present invention is directed to a target substance-detecting apparatus comprising: a target substance-detecting element of which absorbance varies according to a wavelength of an incident light; a light irradiation section for irradiating the target substance-detecting element with a linearly polarized light which is the incident light, while changing the wavelength of the incident light; a polarizing section that separates a transmitted light when the target substance-detecting element has been irradiated with the incident light into a first polarized light and a second polarized light having a vibration direction different from that of the first polarized light; a first light-receiving section for outputting a first signal according to intensity of the first polarized light, and a second light-receiving section for outputting a second signal according to intensity of the second polarized light; a memory device for storing a plurality of standard data including first absorbance based on the intensity of the first polarized light and second absorbance based on the intensity of the second polarized light, which correspond to a plurality of rotation angles of the target substance-detecting element respectively, according to the respective rotation angles; and a data-correcting section which determines a peak of the first absorbance by measuring the first absorbance from the first signal, determines a peak of the second absorbance by measuring the second absorbance from the second signal, specifies the rotation angle from the plurality of the standard data which are stored in the memory device based on the respective peak values, and calculates a correction factor formed from the peak values of the first absorbance, which are stored in the memory device corresponding to the rotation angle, and the maximum peak value of the first absorbance, which is stored in the memory device.

The present invention is directed to a method for detecting a target substance with the use of a target substance-detecting element of which the absorbance varies according to a wavelength of an incident light, comprising: irradiating the target substance-detecting element with a linearly polarized light which is the incident light, while changing the wavelength of the light; separating a transmitted light when the target substance-detecting element has been irradiated with the incident light into a first polarized light and a second polarized light having a vibration direction different from that of the first polarized light; and determining a peak of first absorbance by measuring the first absorbance based on intensity of the first polarized light, determining a peak of second absorbance by measuring the second absorbance based on intensity of the second polarized light, maximizing the peak value of the first absorbance and minimizing the peak value of the second absorbance based on the respective peak values, and then detecting the target substance.

The method for detecting the target substance can comprise changing the peak values of the first absorbance and the second absorbance by rotating the target substance-detecting element. The method for detecting the target substance can comprise rotating the target substance-detecting element until the peak value of the second absorbance becomes smaller than a predetermined threshold value, after the first absorbance and the second absorbance have been measured. The method for detecting the target substance can comprise producing a plurality of standard data including the first absorbance based on the intensity of the first polarized light and the second absorbance based on the intensity of the second polarized light, which correspond to a plurality of rotation angles of the target substance-detecting element respectively, according to each of the rotation angles; and determining an angle to which the target substance is rotated by measuring the first absorbance and the second absorbance to determine each of the peak values, and using the peak value of the first absorbance, the peak value of the second absorbance and the plurality of the standard data.

The present invention is directed to a method for detecting a target substance with the use of a target substance-detecting element of which absorbance varies according to a wavelength of an incident light, comprising: irradiating the target substance-detecting element with a linearly polarized light which is the incident light, while changing the wavelength of the incident light; separating a transmitted light when the target substance-detecting element has been irradiated with the incident light into a first polarized light and a second polarized light having a vibration direction different from that of the first polarized light; producing a plurality of standard data including first absorbance based on intensity of the first polarized light and second absorbance based on intensity of the second polarized light, which correspond to a plurality of rotation angles of the target substance-detecting element respectively, according to each of the rotation angles; and determining a peak value of the first absorbance by measuring the first absorbance based on the intensity of the first polarized light, determining a peak value of the second absorbance by measuring the second absorbance based on the intensity of the second polarized light, specifying the rotation angle from the respective peak values and the plurality of the standard data, and calculating a correction factor formed from the peak value of the first absorbance corresponding to the rotation angle and the maximum peak value of the first absorbance in the plurality of the standard data; and then detecting the target substance.

Further features of the present invention will become apparent from the following description of examples with reference to the attached drawings.

DESCRIPTION OF THE EMBODIMENTS

Embodiments according to the present invention will now be described below with reference to the drawings.

Here, particular embodiments will be described in detail, but the present invention is not limited to the embodiments described here.

Embodiment 1

A target substance-detecting apparatus according to the present embodiment will now be described.

Figure 1:
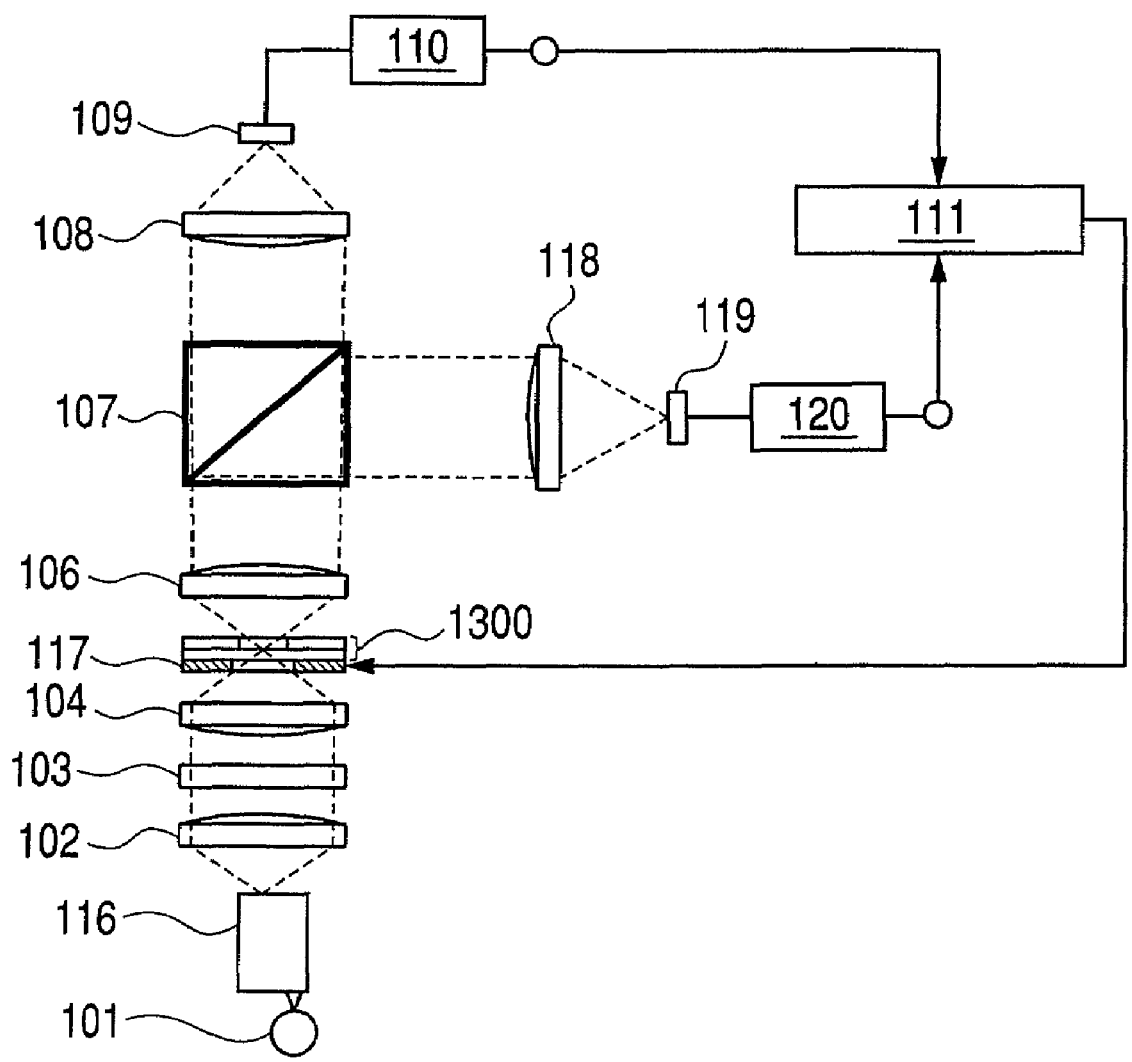
FIG. 1 is a schematic view illustrating one configuration example of a target substance-detecting apparatus according to Embodiment 1 and Example 1.

FIG. 1 is a schematic view illustrating one configuration example of a target substance-detecting apparatus according to the present embodiment.

When a light source 101 emits a light, a monochrometer 116 takes out only a light having a set wavelength. The light is converted into a linearly polarized light from a circularly polarized light through a group of lenses (collector lens 102 and condenser lens 103) and a polarizer 104, and is emitted toward a target substance-detecting element 105 comprised in reaction kit 1300. The above described light source 101, monochrometer 116, collector lens 102, condenser lens 103 and polarizer 104 are inclusively referred to as a light irradiation section. A reaction kit 1300 has a reaction well 1301, the target substance-detecting element 105 existing inside the reaction well 1301, and a reaction well cover 1302 which covers the reaction well, as is illustrated in FIG. 4. The reaction well 1301 and the reaction well cover 1302 can have a coating layer so that the surface of the reaction well 1301 and the reaction well cover 1302 may absorb the target substance as little as possible. The reaction kit 1300 is provided with a rotation mechanism 117, and can be rotated. The rotation mechanism 117 also has a function as a sample stage.

When irradiating a target substance-detecting element 105 with a light, an emitted light from the target substance-detecting element 105 is generated. The emitted light is separated by a polarization beam splitter 107 through an objective lens 106. At this time, the transmitted light is separated into a polarized light (first polarized light) of which the polarized component is parallel to an incident light and a polarized light (second polarized light) of which the polarized component is perpendicular to the incident light. When the target substance-detecting element 105 is irradiated with the light, the target substance-detecting element 105 generates an output light. The output light emitted from the target substance-detecting element 105 is separated by a polarization beam splitter 107 through an objective lens 106. At this time, the output light is separated into a polarized light (first polarized light) of which the polarized component is parallel to an incident light and a polarized light (second polarized light) of which the polarized component is perpendicular to the incident light. The output light to be emitted from the target substance-detecting element 105 includes a transmitted light, a reflected light, and a scattered light, but among them, the transmitted light can be used. In the example, an example using the transmitted light is shown. In addition, the light having passed the objective lens 106 is divided into a first polarized light and a second polarized light by a beam splitter in the present embodiment, but it is also possible to divide the light having passed the objective lens 106 into a first light and a second light by a dividing splitter without using the beam splitter, and pass respective lights through polarizers having different polarized light directions from each other to form the first polarized light and the second polarized light. In the present embodiment, the beam splitter is occasionally referred to as a light-polarizing section, but when the above described dividing splitter is used, the polarizers having the different polarized light directions from each other may be referred to as the light-polarizing section.

The first polarized light is received by a photo detector 109 as the first light-receiving section through a lens 108, and is converted into a signal (first signal) corresponding to the intensity of the first polarized light. The first signal is amplified by an amplifier 110, and is input into a signal processing section 111.

The second polarized light is received by a light receiving element 119 as the second light-receiving section through a lens 118, and is converted into a signal (second signal) corresponding to the intensity of the second polarized light. The second signal is amplified by an amplifier 120, and is input into the signal processing section 111.

The signal processing section 111 measures the absorbance of the first and second polarized lights based on the signals respectively input from the amplifier 110 and the amplifier 120.

In this way, the signal processing section 111 sequentially measures the absorbance of the target substance-detecting element 105 for the incident light of which the wavelength has been changed by the monochrometer 116, and as a result, measures a light absorbance spectrum which shows a relationship between the wavelength of the incident light and its absorbance.

In the present embodiment, the light source 101 is not limited in particular, as long as it has stable light intensity. For instance, a halogen lamp can be used as the light source 101.

In addition, the monochrometer 116 can have a wavelength resolution power of approximately 1 nm, and can work in a wavelength range of visible light to near infrared rays (400 to 1500 nm).

The collector lens 102 and the condenser lens 103 can have a structure with a small NA (numerical aperture) so that the target substance-detecting element 105 can be irradiated with a light containing as many parallel components as possible.

In addition, the polarizer 104 can have a contrast ratio of 1:100 or more in the whole measuring wavelength range.

The objective lens 106 can focus on the target substance-detecting element 105 from above a cover which covers the target substance-detecting element 105 for a channel, and can employ a group of lenses having a cover-glass lens correction mechanism.

The polarization beam splitter 107 can separate light with a contrast ratio of 1:100 or more in the whole measuring wavelength.

In addition, the lens 108 and the lens 118 are not limited in particular, as long as they can focus on each light receiving element while eliminating the effect of chromatic aberration as much as possible.

When the light receiving element 109 and the light receiving element 119 are not particularly limited, as long as they have sensibility in the wavelength range of visible light to near infrared rays (400 to 1500 nm). For instance, a photodetector employing Si and InGaAs and so forth is used as the light receiving element.

The amplifier 110 and the amplifier 120 can have a superior signal to noise ratio. In order to improve the signal to noise ratio, the amplifier 110 and the amplifier 120 may synchronously detect the signal.

Subsequently, the target substance-detecting element 105 will be described.

FIGS. 2A and 2B and FIGS. 3A to 3D are schematic views illustrating one example of a shape of the target substance-detecting element 105.

As is illustrated in FIG. 2, the target substance-detecting element 105 has a transparent substrate 1402, a metal structure 1401 which is disposed on the surface of the transparent substrate and causes plasmon resonance with incident light, and a target substance-capturing body (not shown) existing on the surface of the metal structure. Here, the meaning of being transparent is that the substrate has sufficient optical transparency for measurement. The substrate can have such absorbance as to be ½ or less of respective peaks of the first absorbance and the second absorbance which will be described below, in the vicinity of wavelengths of the peaks of the respective absorbances.

In addition, the target substance-detecting element 105 has such a shape as to show anisotropy in a plane perpendicular to incident light. Specifically, the shape can be a rectangle as illustrated FIG. 2, multimer dots as illustrated in FIG. 3, or metal structure. In addition, a direction to be used for detecting the target substance is defined as a main axis in the target substance-detecting element 105. For instance, when the target substance-detecting element is the rectangular shape, a longitudinal direction thereof is a main axis. In the case of a twin dot, a direction in which dots are combined is a main axis.

The incidence angle is defined by an angle formed by a vibration direction of the incident light and the main axis. The target substance-detecting apparatus gives the maximum value of absorbance at zero degree of the incidence angle, and the minimum one at 90 degree thereof. Namely, the incidence angle as an angle formed by the main axis of the metal structure and the vibration direction of the irradiating light is preferably controlled by the controlling section so as to be minimized.

The target substance-capturing body owned by the target substance-detecting element 105 is specifically combined with a target substance to form a conjugate. Here, the target substance which is included in a specimen is roughly classified into non-biological matter and biological matter.

The non-biological matter having a great industrial utility value includes PCBs (Polychlorinated Biphenyl) having different number/position of substituent chlorine, dioxins, and an endocrine disrupter which is a so-called environmental hormone.

The biological matter includes nucleic acid, protein, sugar chain, lipid and a compound thereof.

In more detail, the biological matter includes a biomolecule selected from nucleic acid, protein, sugar chain, lipid and the like. Examples of such a biological matter includes deoxyribonucleic acid, ribonucleic acid, an aptamer, a gene, a chromosome, a cell membrane, a virus, an antigen, an antibody, lectin, hapten, hormone, a receptor, an enzyme, peptide, sphingo sugar and sphingolipid.

In the present invention, bacteria and cell themselves which produce the above described biological matter also can be the target substance.

A method for producing the target substance-detecting element 105 will now be described.

The method for producing the target substance-detecting element 105 has only to form a desired pattern, and is not limited in particular. For instance, the target substance-detecting element 105 may be produced by using any of the techniques such as electron beam lithography, photolithography, X-ray lithography and a nano-imprint technique.

Furthermore, the target substance-detecting element 105 may be produced with a self-organizing method. In addition, when forming the pattern by copying, the target substance-detecting element 105 may be produced through forming the pattern with etching and lift-off techniques.

Figure 2A:
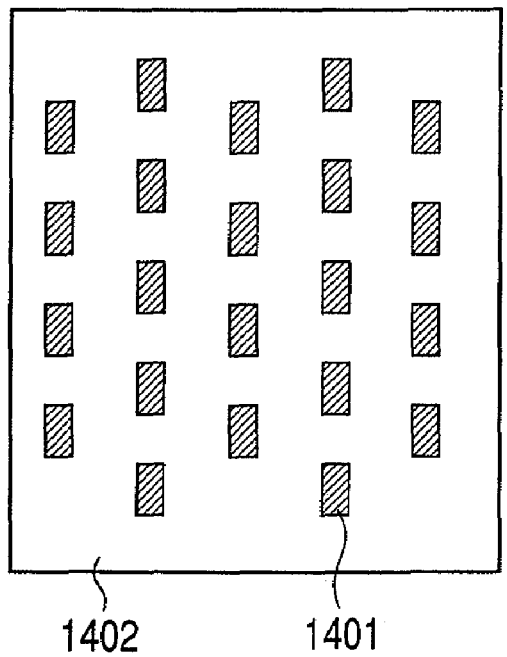
FIGS. 2A and 2B are schematic views respectively illustrating one example of a shape of a target substance-detecting element.
Figure 2B:
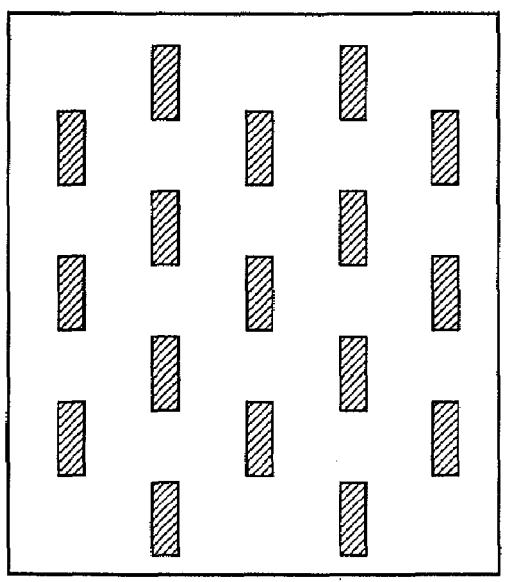
Figure 3A:
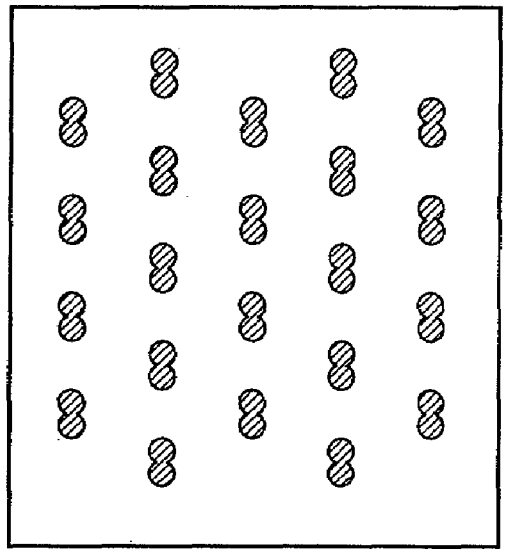
FIGS. 3A, 3B, 3C and 3D are schematic views respectively illustrating one example of a shape of a target substance-detecting element.
Figure 3B:
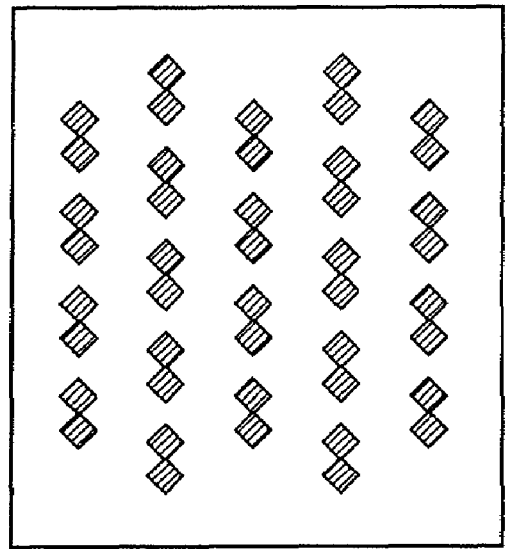
Figure 3C:
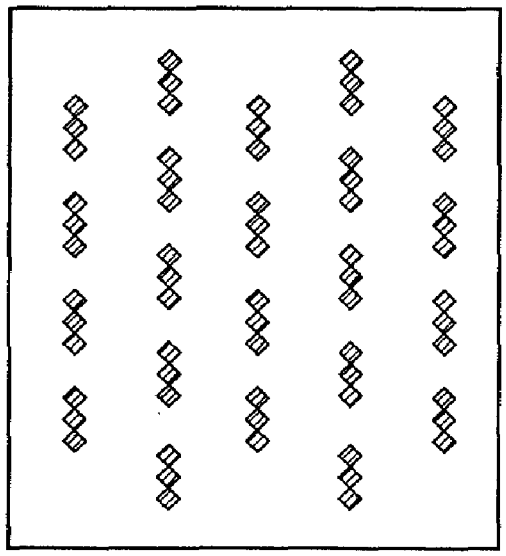
Figure 3D:
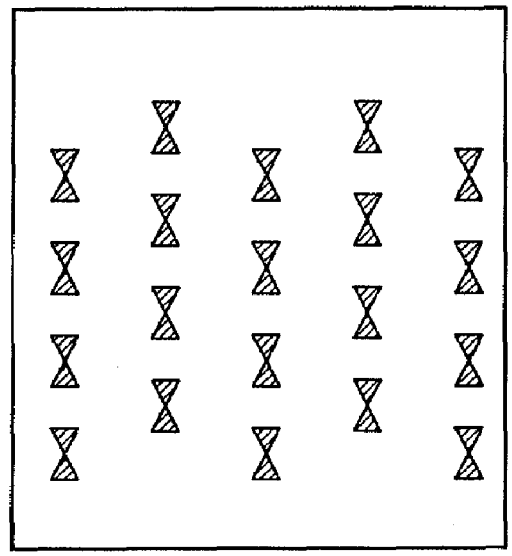

Next, an operation of a target substance-detecting apparatus in the first embodiment after having measured an absorbance spectrum will be described. Here, a rectangular shape is used as a shape of a target substance-detecting element 105, as is illustrated in FIG. 2A.

Figure 5:
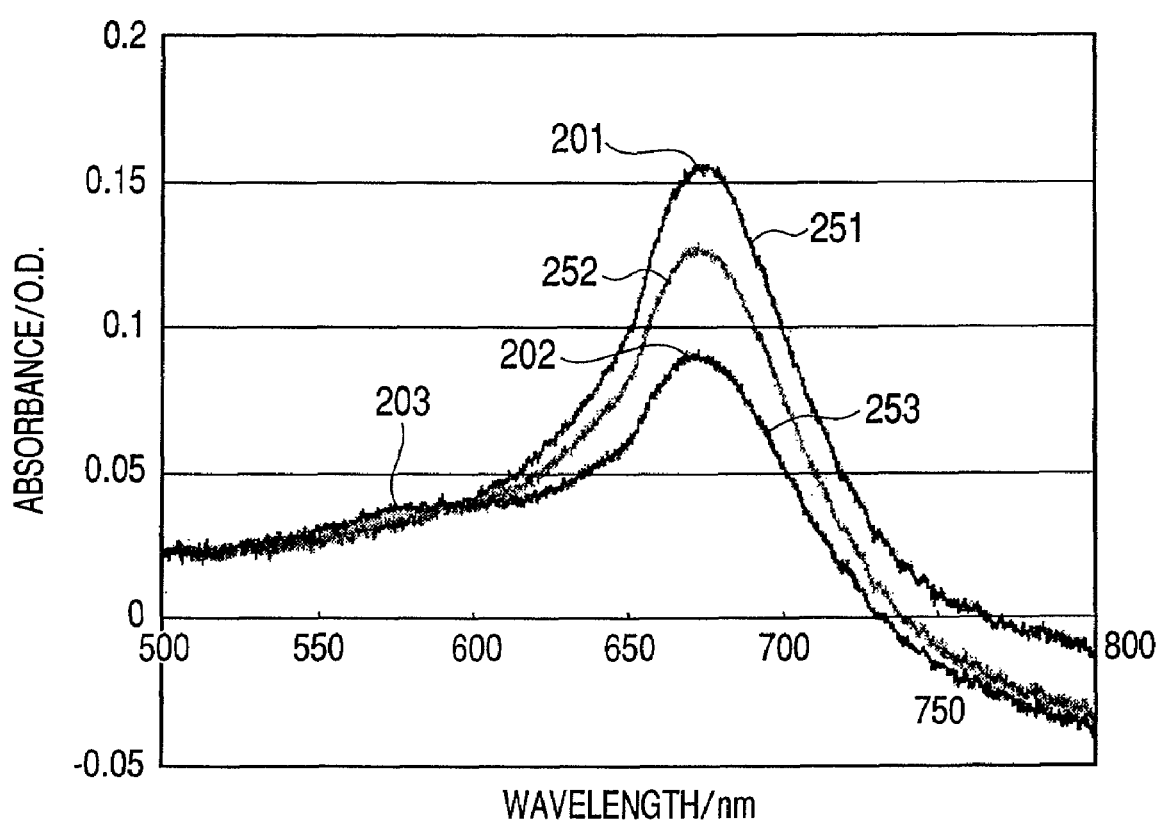
FIG. 5 is a graph illustrating one example of the absorbance spectrum of a target substance-detecting element.

FIG. 5 is a graph illustrating one example of the absorbance spectrum of the target substance-detecting element 105. In FIG. 5, a horizontal axis represents a wavelength of incident light, and a vertical axis represents the absorbance of the incident light.

FIG. 5 illustrates absorbance spectra 251, 252 and 253 when an angle (angle of incidence) formed by a vibration direction of the incident light and a main axis of the target substance-detecting element 105 is 0 degree, approximately 15 degrees and approximately 45 degrees, respectively.

When the angle of incidence is 0 degree, that is to say, when the vibration direction of the incident light is parallel to the main axis of the target substance-detecting element 105, a peak 201 of the absorbance (first absorbance) of a first polarized light remarkably appears, as is illustrated in FIG. 5. Here, the peak means a point at which the absorbance has a local maximum value. The actual wavelength and absorbance of the peak can be decided, for instance, by a method of carrying out a fitting operation based on a sampling point and calculating a peak position of the fitting function as a peak.

When the angle of incidence is 45 degrees, a peak 203 of the absorbance (second absorbance) of a second polarized light appears together with a peak 202 of the first absorbance, as is illustrated in FIG. 5. The value (absorbance) of the peak 202 can be occasionally smaller than the value (absorbance) of the peak 203.

A concentration of the target substance and a reaction time of the target substance with a capturing body are measured based on a shifted amount of the wavelength at the peak of the first absorbance. Accordingly, when the peak value of the first absorbance decreases, a signal-to-noise ratio of a signal output from the light receiving element 109 is aggravated, which results in lowering the detection sensibility for the target substance. In addition, the peak value varies due to the aggravation of the signal-to-noise ratio, which results in lowering the detection sensibility for the target substance.

For this reason, the peak values need to be adjusted so that the peak value of the first absorbance is maximized and the peak value of the second absorbance is minimized. For instance, when the angle of incidence is 15 degrees or 45 degrees in FIG. 5, i.e. when the first and second absorbances exist, the peak value of the first absorbance is increased, and the peak value of the second absorbance is decreased.

Figure 6:
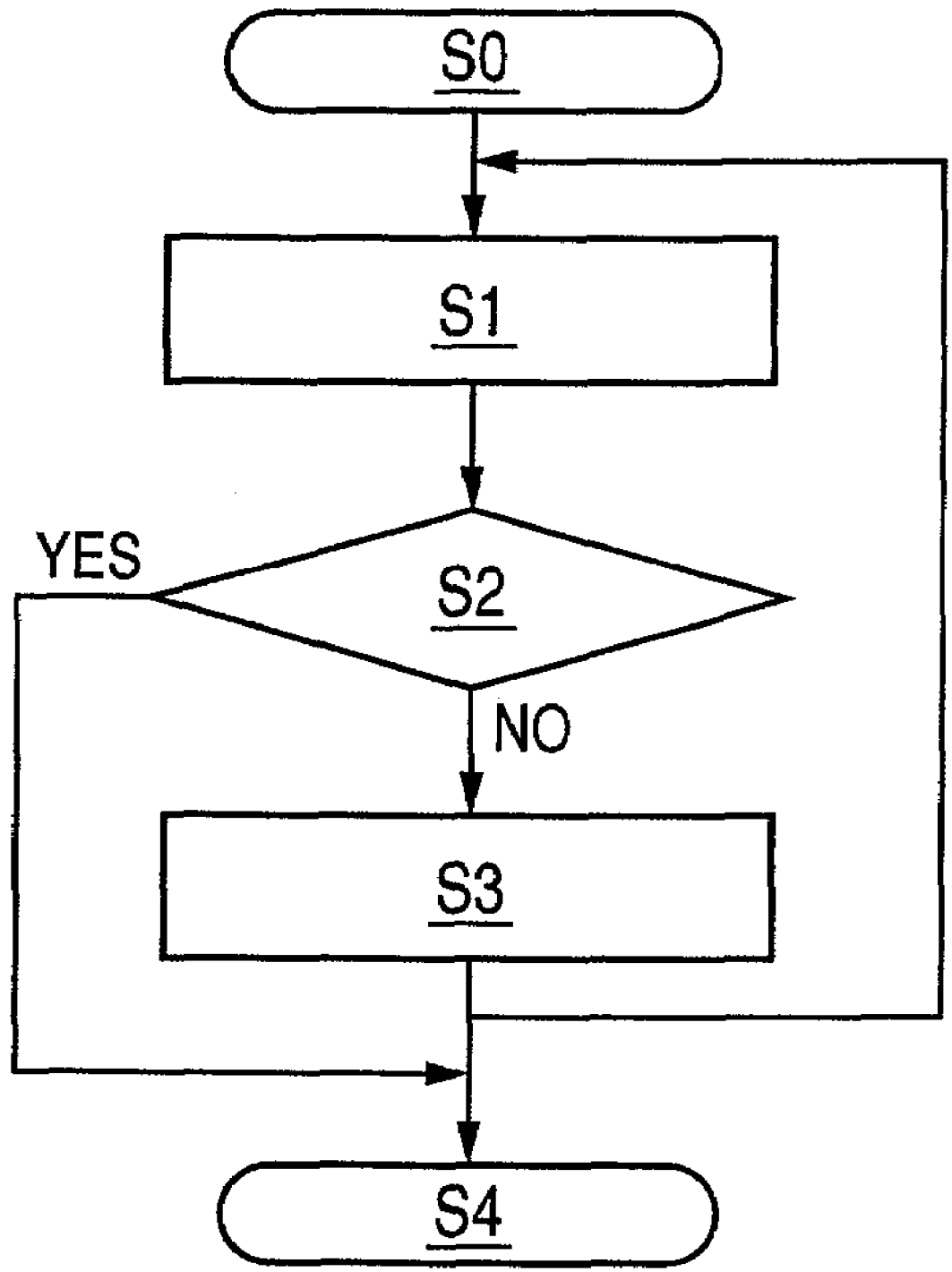
FIG. 6 is a flow chart illustrating an operation procedure for adjusting an angle of incidence in Embodiment 1 and Example 1.

FIG. 6 is a flow chart illustrating an operation procedure for adjusting an angle of incidence in the present embodiment. Reference character S0 denotes the start, and reference character S4 denotes the end.

At first, a signal processing section 111 in FIG. 1 measures an absorbance spectrum of a target substance-detecting element 105 comprised in reaction kid 1300 based on signals output from a light receiving element 109 and a light receiving element 119 (step S1).

Figure 7:
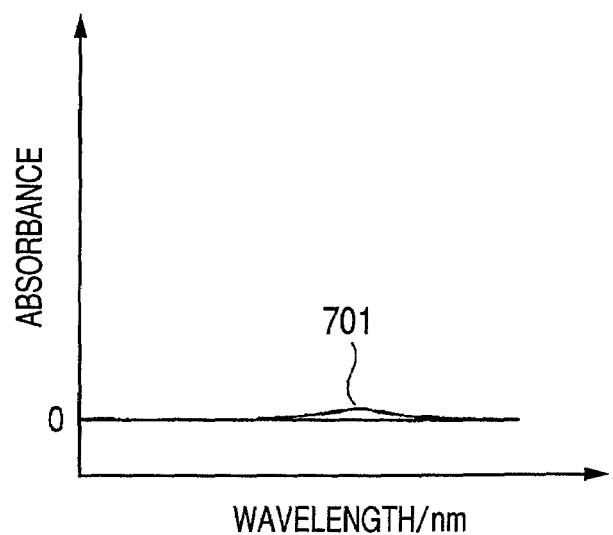
FIG. 7 is a graph illustrating one example of an absorbance spectrum corresponding to the second absorbance.

At this time, when the angle of incidence is not 0 degree, a peak value 701 is measured in the absorbance spectrum based on a second polarized light, as is illustrated in FIG. 7, for instance.

Subsequently, the signal processing section 111 compares the peak value of second absorbance with a predetermined threshold value (step S2). Here, preferably, the threshold value is appropriately set in a range of $1/10$ to $1/10000$ of the peak value of first absorbance which is measured when the angle of incidence is 0 degree.

When the peak value of the second absorbance is larger than the threshold value, the signal processing section 111 outputs a control signal to make a mechanism 117 rotate the target substance-detecting element 105 by only a predetermined angle (step S3). The reaction kit 1300 rotates so that the angle of incidence to target substance-detecting element 105 changes.

After the mechanism 117 has rotated the target substance-detecting element 105 comprised in reaction kit 1300, the signal processing section 111 conducts the operations of the step S1 and step S2 again. When the peak value of the second absorbance is larger than the threshold value, the signal processing section 111 conducts the operation of the step S3 again.

The operations of the step S1 to the step S3 are repeated until the peak value of the second absorbance becomes smaller than the threshold value.

In this way, the angle of incidence is adjusted into an angle at which plasmon resonance remarkably appears which occurs in the target substance-detecting element based on a measurement result of the absorbance. Thereby, a detection accuracy for the target substance is improved.

In the present invention, the combination of the signal processing section and the rotation mechanism is occasionally referred to as a control section.

Embodiment 2

A target substance-detecting apparatus according to the present embodiment can detect a target substance with high accuracy and at a high speed.

Figure 8:
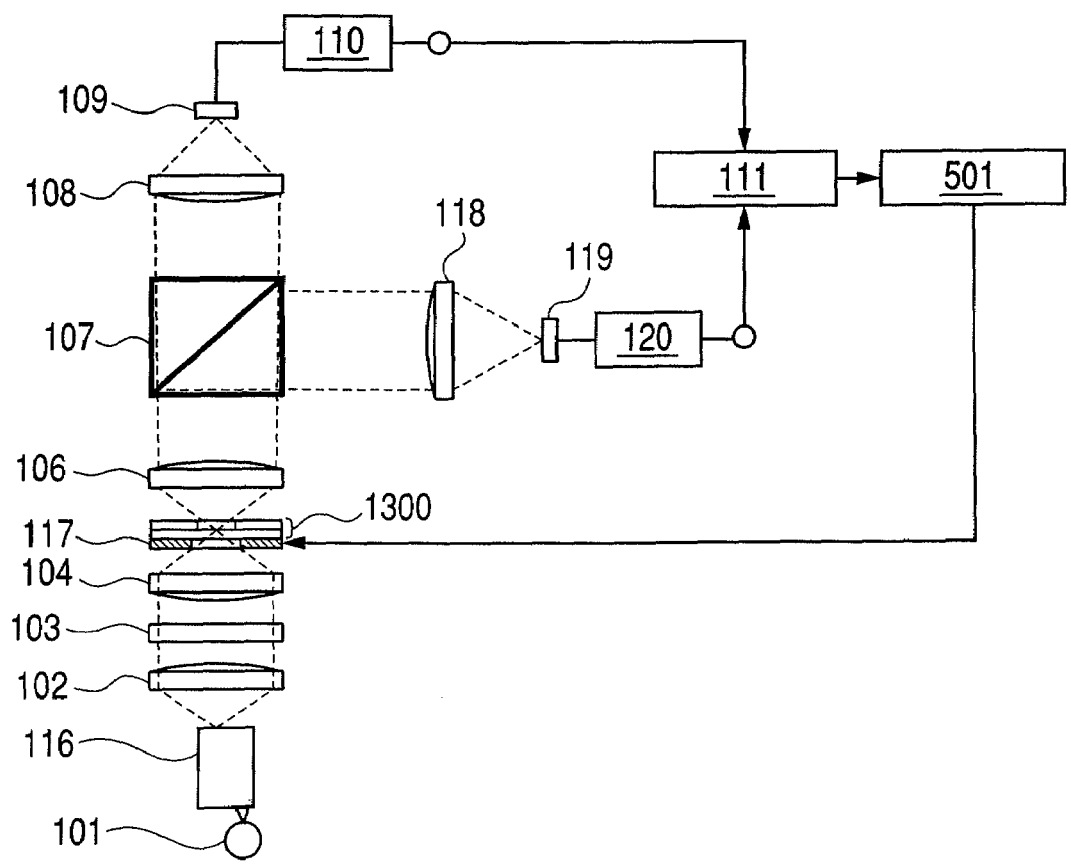
FIG. 8 is a schematic view illustrating one configuration example of a target substance-detecting apparatus according to Embodiment 2 and Example 2.

FIG. 8 is a schematic view illustrating one configuration example of a target substance-detecting apparatus according to the present embodiment. Configurations similar to the ones described in embodiment 1 are affixed with the same reference numerals, and the detailed description will be omitted.

The target substance-detecting apparatus of the present embodiment, as is illustrated in FIG. 8, is provided with a data processing section (A) 501 added to the target substance-detecting apparatus of Embodiment 1, as a new configuration.

The data processing section (A) 501 has a configuration that includes a memory device such as a memory, for instance.

The memory device owned by a data processing section (A) 501 stores standard data of the first absorbance based on the intensity of the first polarized light and the second absorbance based on the intensity of the second polarized light, according to each of the angles of incidence of lights incident on the above described target substance-detecting element.

The data processing section (A) 501 outputs a control signal for making the rotation mechanism 117 rotate the target substance-detecting element 105.

An operation of the target substance-detecting apparatus of the present embodiment will now be described below. Also, since the operation prior to a measurement of the absorbance spectrum of the target substance-detecting element 105 is similar to the operation described in Embodiment 1, the description will be omitted.

Figure 9:
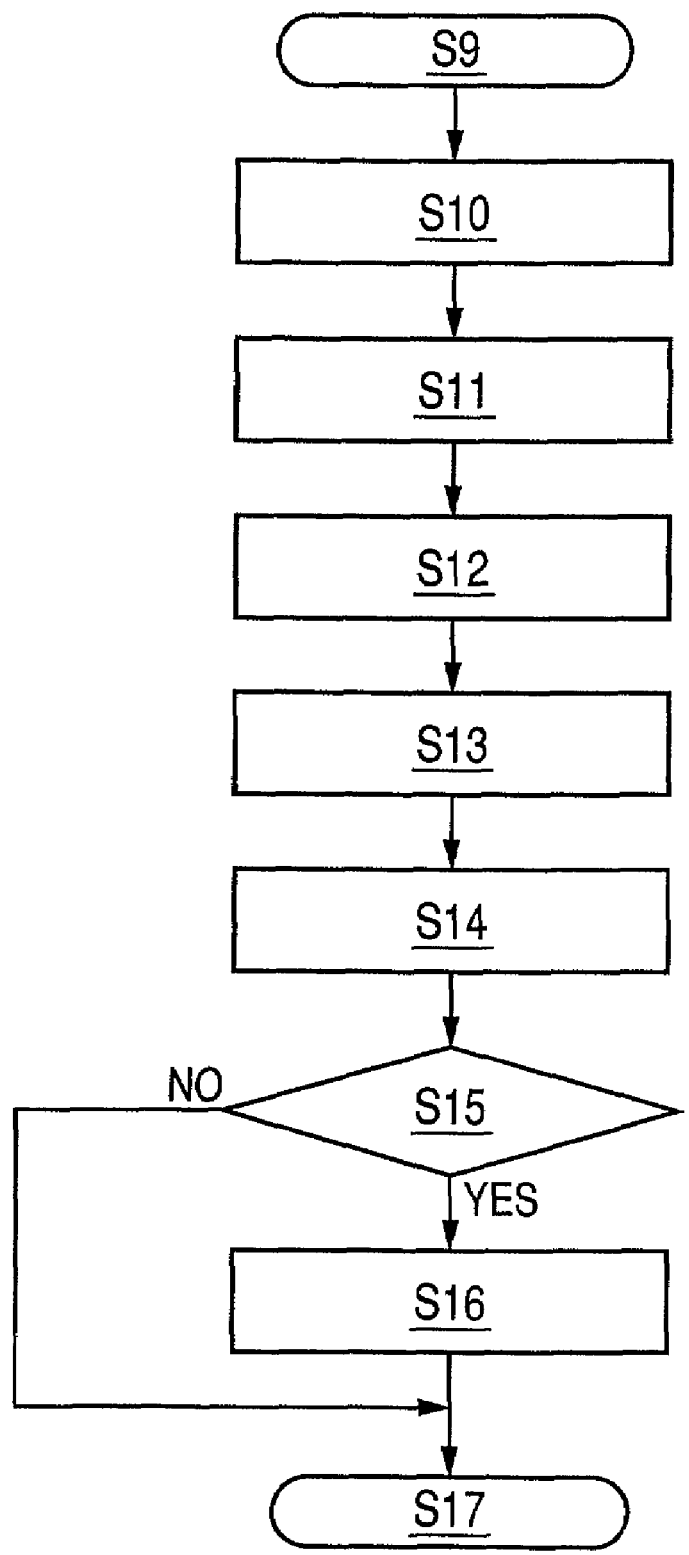
FIG. 9 is a flow chart illustrating an operation procedure for adjusting an angle of incidence in Embodiment 2 and Example 2.

FIG. 9 is a flow chart illustrating an operation procedure for adjusting an angle of incidence in the present embodiment. Reference character S9 denotes the start, and reference character S17 denotes the end.

At first, a signal processing section 111 measures an absorbance spectrum of the target substance-detecting element 105 based on signals output from a light receiving element 109 and a light receiving element 119, and outputs the absorbance spectrum to the data processing section (A) 501 (step 10).

Subsequently, the data processing section (A) 501 specifies the angle of incidence with the use of a plurality of standard data which is stored in a memory device, and the values of the absorbance of the first peak and the second peak of the obtained absorbance spectrum (step S11). Then, the data processing section (A) 501 calculates an angle Δθ at which the target substance-detecting element 105 is rotated, in order to adjust the angle of incidence to the optimal angle for detecting the target substance in the standard data (i.e., the angle enabling the peak of the first absorbance to be maximized and the peak of the second absorbance to be minimized in the standard data), with the use of a plurality of standard data stored in a memory device (step S12).

After having calculated the angle Δθ, the data processing section (A) 501 outputs a control signal to make the rotation mechanism 117 rotate the target substance-detecting element 105 by the angle Δθ (step S13).

After the rotation mechanism 117 has rotated the target substance-detecting element 105 by the angle Δθ, the target substance-detecting element 105 is irradiated with the incident light again.

Then, the signal processing section 111 measures the absorbance spectrum of the target substance-detecting element 105 again, and outputs the absorbance spectrum to the data processing section (A) 501 (step S14).

Subsequently, the data processing section (A) 501 determines whether a direction of rotation is in an opposite direction or not by comparing the absorbance spectrum to the absorbance corresponding to the angle of incidence at which the peak value of the first absorbance is maximized, among the data stored in the memory device (step S15).

When the direction of the rotation is opposite to the above direction, the data processing section (A) 501 outputs a control signal to make the rotation mechanism 117 rotate the target substance-detecting element 105 by an angle −2 Δθ (step S16).

In this way, the angle of incidence is adjusted on the basis of the measurement result of the absorbance so as to remarkably show the plasmon resonance occurring in the target substance-detecting element. Since the number of rotation times of the target-substance-detecting element 105 is more likely to be reduced in the present embodiment than that of the target substance-detecting apparatus described in Embodiment 1, the angle of incidence can be adjusted with higher accuracy and at a higher speed than the apparatus in Embodiment 1.

The data processing section (A) 501 may be set so as to be a memory device provided with only the above described memory devices, and the signal processing section 111 may perform the operations of the step S11 to step S16. In this case, the configuration of the data processing section (A) 501 becomes simple.

Embodiment 3

A target substance-detecting apparatus according to the present embodiment can detect a target substance with high accuracy without using a rotation mechanism described in Embodiment 1 and Embodiment 2.

Figure 10:
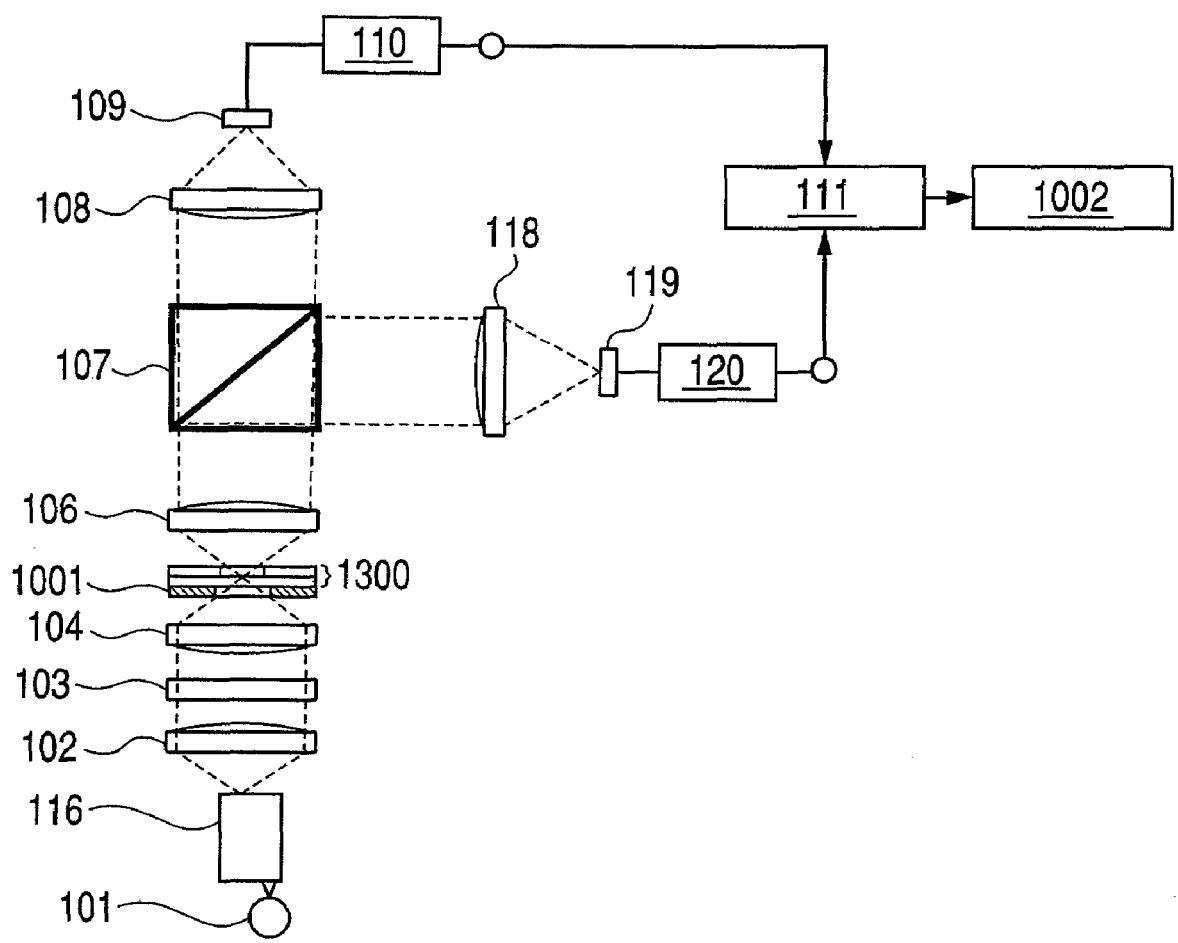
FIG. 10 is a schematic view illustrating one configuration example of a target substance-detecting apparatus according to Embodiment 3 and Example 3.

FIG. 10 is a schematic view illustrating one configuration example of a target substance-detecting apparatus according to the present embodiment. Configurations similar to the ones described in embodiment 1 are affixed with the same reference numerals, and the detailed description will be omitted.

The target substance-detecting apparatus of the present embodiment, as is illustrated in FIG. 10, is provided with a sample stage 1001 as a substitute for a rotation mechanism 117, and a data processing section (B) 1002, as a new configuration, in comparison with a target substance-detecting apparatus described in Embodiment 1.

The data processing section (B) 1002 has a configuration that includes a memory device such as a memory, for instance.

The memory device of the data processing section (B) 1002 has a plurality of standard data including the first absorbance and the second absorbance of the target substance-detecting element 105 for every rotation angle.

In the next place, an operation of the target substance-detecting apparatus of the present embodiment will now be described. Since the operation prior to a measurement of the absorbance of the target substance-detecting element 105 is similar to the operation described in Embodiment 1, the description will be omitted.

Figure 11:
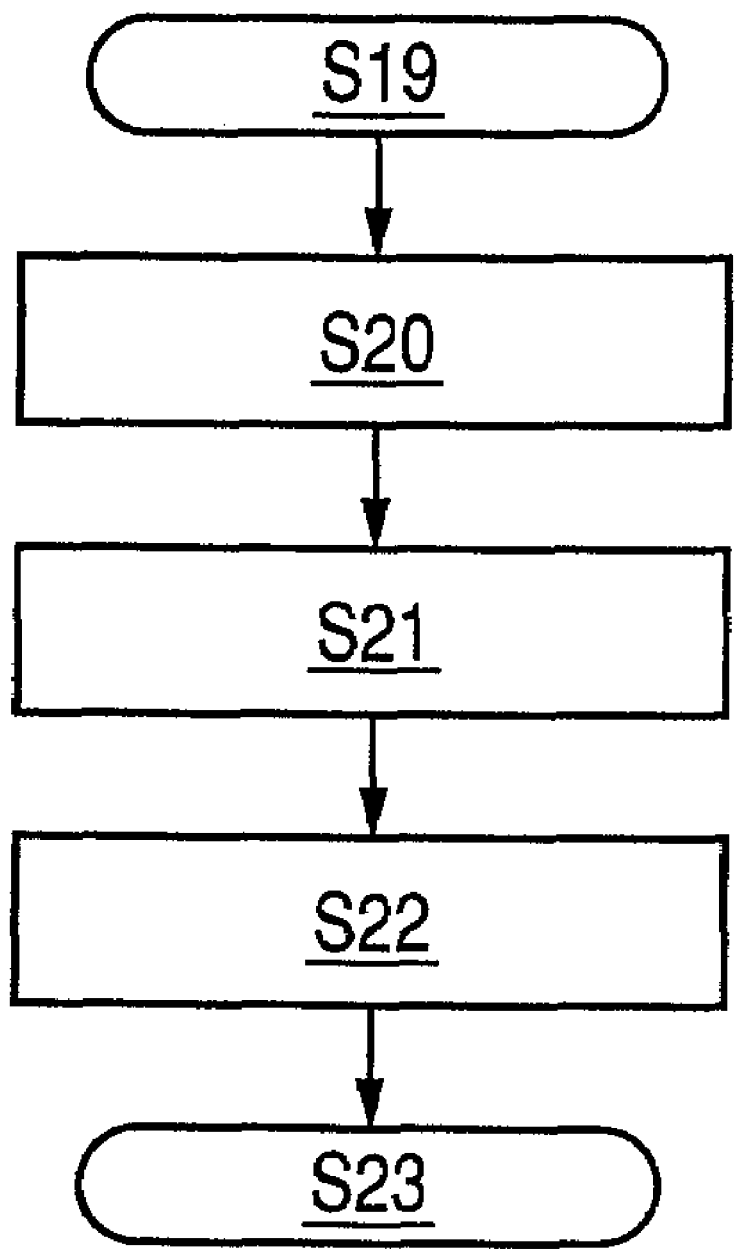
FIG. 11 is a flow chart illustrating an operation procedure for calculating a correction factor in Embodiment 3 and Example 3.

FIG. 11 is a flow chart illustrating an operating procedure for calculating a correction factor in the present embodiment. Reference character S19 denotes the start, and reference character S23 denotes the end.

At first, a signal processing section 111 measures an absorbance spectrum of the target substance-detecting element 105 based on signals output from a light receiving element 109 and a light receiving element 119, and outputs the absorbance spectrum to a data processing section (B) 1002 (step S20).

Subsequently, the data processing section (B) 1002 specifies the angle of incidence with the use of the data which is stored in a memory device comprised in the section 1002 and the values of the absorbance (i.e., the first absorbance (a) and the second absorbance (b)) of the first peak and the second peak of the obtained absorbance spectrum (step S21). Then, the data processing section (B) 1002 determines a correction factor (C) defined by the following Expression (1) with the use of the peak value (the peak value (c) of the first absorbance) of first absorbance in the angle of incidence specified from the standard data stored by the memory device and the maximum value (maximum peak value) of the first absorbance in the standard data (step S22).

In the above description, the maximum peak value corresponds to the peak value of the first absorbance which is measured at the time when the angle of incidence is optimal for detecting the target substance.

$$C=\text{(maximum peak value)}/\text{(peak value }(c)\text{ of the first absorbance)} \quad (1)$$

The data processing section (B) 1002 measures a correction value by making the correction with the following Expression (2) for the measured first absorbance (measured value), when the data showing the absorbance spectrum of the target substance-detecting element on which the target substance is conjugated with a capturing body is input from the signal processing section 111. The symbol (C) described below denotes a correction factor defined in Expression (1).

$$\text{Correction value}=\text{measured value}* \quad (2)$$

The data processing section (B) 1002 may perform smoothing treatment after having measured the correction value. In this case, the signal-to-noise ratio is improved, and the target substance can be detected with high accuracy.

In the above description, the data processing section (B) 1002 may be set so as to be a memory device provided with only the above described memory devices, and the signal processing section 111 may perform the operations of the step S21 to the step S22. In this case, the configuration of the data processing section (B) 1002 becomes simple.

In the next place, the present invention will be described in more detail with reference to Examples. The examples are described with the use of the specific target substance and numeric values so as to have the present invention fully understood, but the examples neither limit the present invention, nor show the optimum value.

Example 1

The present example detects a target substance with the use of a target substance-detecting apparatus illustrated in FIG. 1 described in Embodiment 1.

At first, an optical system used in the target substance-detecting apparatus in the present example will be briefly described. The Kohler illumination which is general as a method for illuminating a microscope is used as an illumination method. A halogen lamp is used for a light source 101, and ML 44 (SOLAR Laser Systems) is used for a monochrometer 116.

Subsequently, a shape of a target substance-detecting element to be used in the present example will be described.

Figure 12A:
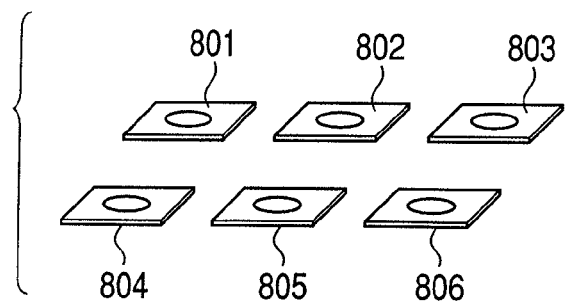
FIGS. 12A, 12B, 12C and 12D are explanatory drawings for describing Example 1 and Example 2.

The target substance-detecting element of the present example has a shape of a rectangular solid of which the length is 50 nm, the width is 100 nm and the thickness is 20 nm. Furthermore, a target substance sensor in the present example has a plurality of target substance-detecting elements of the rectangular solids disposed so that the vertical pitch is 600 nm and the horizontal pitch is 750 nm. FIG. 12D is one example of a secondary electron image 800 of the target substance-detecting elements in FIG. 12A.

When observing a biological reaction such as a conjugation of an antigen with an antibody, it is possible to detect the same reaction through a plurality of the target substance sensors, and statistically process the data, in order to suppress a reaction of a biological substance. For the purpose, in the present example, the same antigen-antibody reaction is observed with the use of six target substance sensors 801 to 806, as is illustrated in FIG. 12A.

In the present example, IgE (immuno-globulin E) antigen was used as the target substance.

A method of detecting the target substance of the present example will now be described below.

Figure 4A:
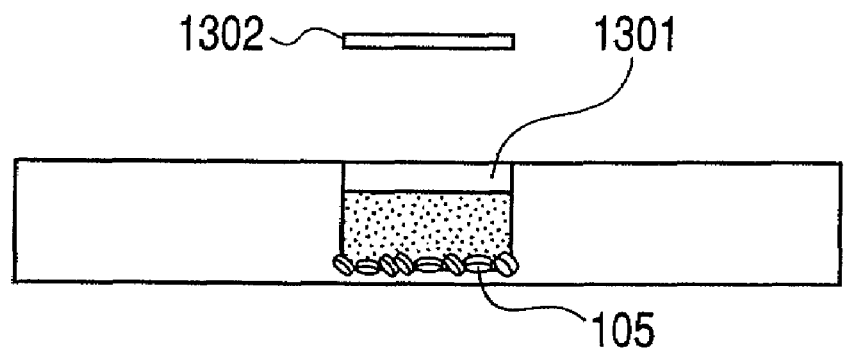
FIGS. 4A and 4B are views for describing a reaction kit.
Figure 4B:
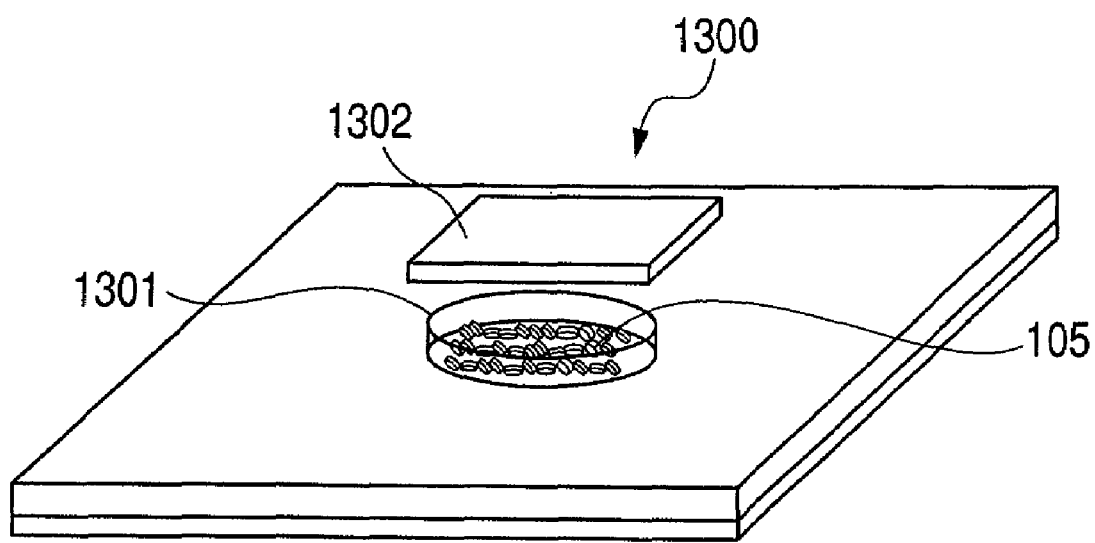

Firstly, the target substance-detecting element is attached to a reaction well 1301 as illustrated in FIGS. 4A and 4B, and the anti-IgE antibody is immobilized on the target substance-detecting element.

Then, the target substance-detecting apparatus measures an absorbance spectrum of the target substance-detecting element on which the anti-IgE antibody is immobilized, as having been described in Embodiment 1. Furthermore, the adjustment of the angle of incidence for enabling the peak of the first absorbance to be maximized and the peak of the second absorbance to be minimized is carried out according to an operation procedure illustrated in FIG. 6.

After the adjustment for the angle of incidence has been finished, a buffer solution which has been adjusted to an optimal pH value for detecting the IgE antigen is injected into the reaction well 1301 to clean the reaction well 1301 and the target substance-detecting element.

Subsequently, 100 μL of a specimen solution containing the IgE antigen is injected into the reaction well 1301 by a micropipetter. Then, an antigen-antibody reaction occurs in the reaction well 1301.

When two hours has passed after the antigen-antibody reaction had started, the specimen solution is extracted with a micropipetter, and an IgE antigen which is non-specifically absorbed by the antibody is washed off by the buffer solution.

After the IgE antigen has been washed, the buffer solution is injected again, and an absorbance spectrum of the target substance-detecting element on which the antigen-antibody reaction has been performed is measured. Then, an absorbance spectrum corresponding to the first absorbance of the target—substance-detecting element in each target substance sensor can be obtained, as is illustrated in FIG. 12C.

Figure 12B:
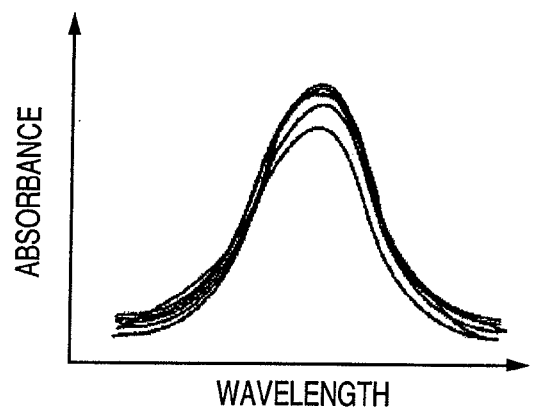
Figure 12C:
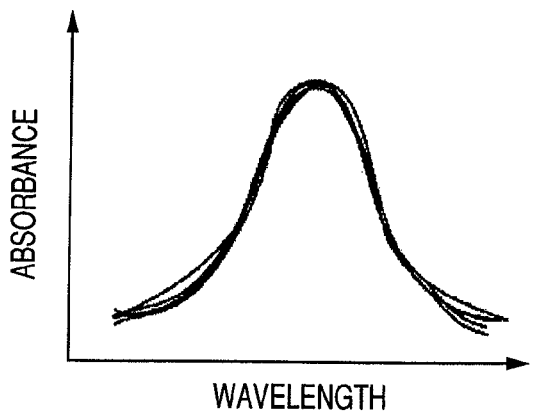
Figure 12D:
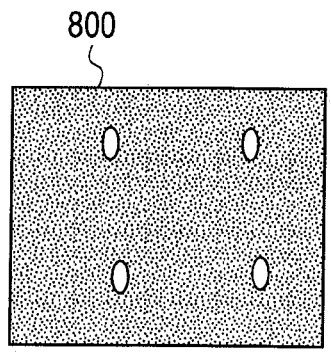

FIG. 12B illustrates one example of the absorbance spectrum corresponding to the first absorbance of the target substance-detecting element in each target substance sensor, when the angle of incidence has not been adjusted. In this case, it is understood that peak values of the absorbance vary compared to those in FIG. 12C.

In the present example, when the concentration of the target substance changes, a wavelength (wavelength of peak)

is shifted at which the absorbance forms a peak value. Then, the absorbance spectrum as is illustrated FIGS. 12B and 12C is measured every time when the concentration has been changed, and is analyzed with a peak fitting technique, for instance, by using a software. As a result, graphs as are illustrated FIGS. 13A and 13B are obtained.

Figure 13A:
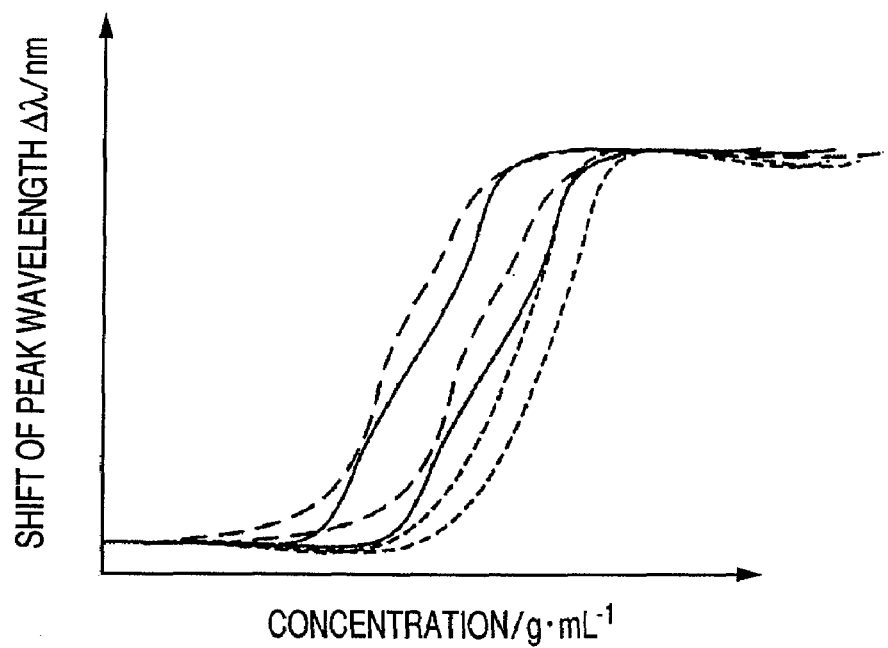
FIGS. 13A and 13B are explanatory drawings for describing Example 1 and Example 2.
Figure 13B:
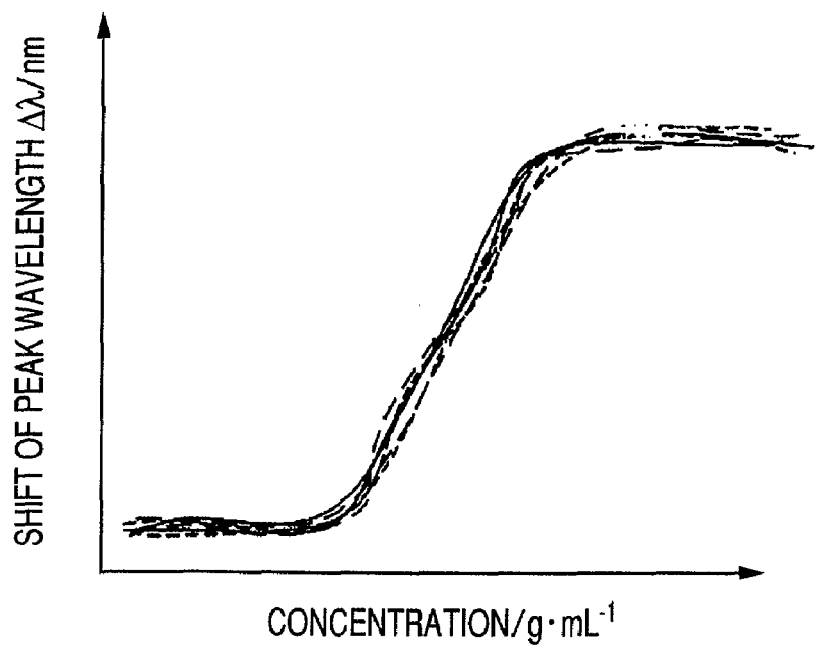

FIGS. 13A and 13B illustrate each properties of six target substance-detecting apparatus. FIG. 13B illustrates the graph obtained when the angle of incidence has been adjusted as has been described in Embodiment 1, and FIG. 13A illustrates the graph obtained when the angle of incidence has not been adjusted. When comparing FIG. 13A with 13B, it can be confirmed that a variation of a shifted amount for a particular concentration is reduced by adjusting the angle of incidence. Thereby, the concentration of the target substance can be detected with high accuracy.

Example 2

In the present example, a target substance-detecting apparatus as is illustrated in FIG. 8 described in Embodiment 2 is used for detecting a target substance. The target substance detected in the present example and the target substance sensor are similar to the ones described in Example 1.

Figure 14A:
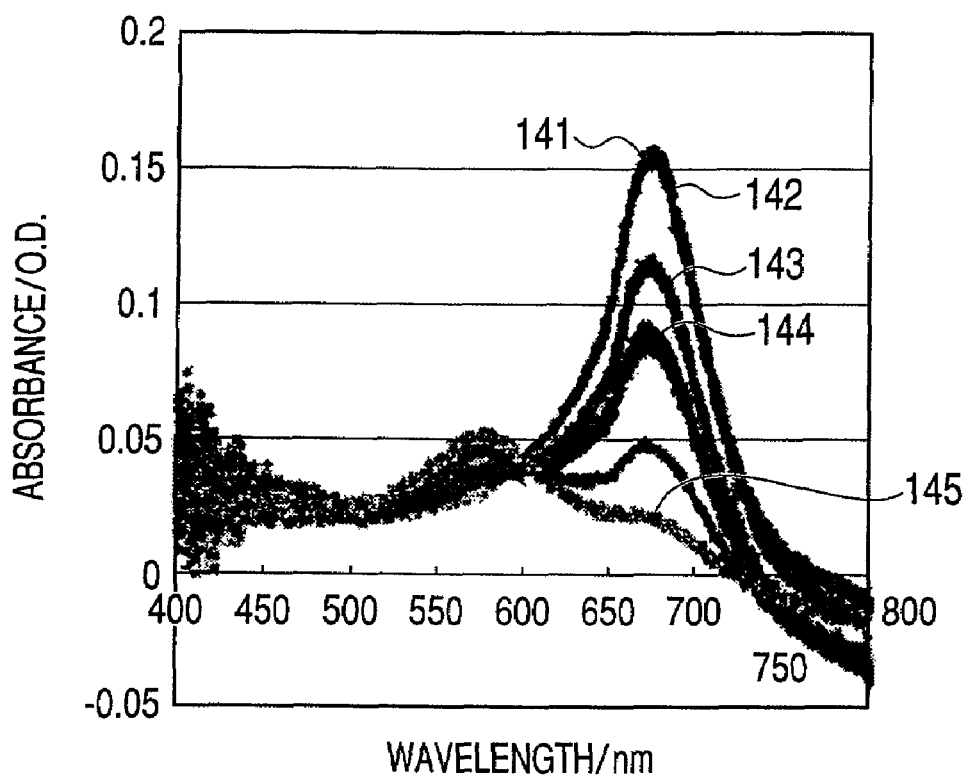
FIGS. 14A and 14B are explanatory drawings for describing Example 2 and Example 3.
Figure 14B:
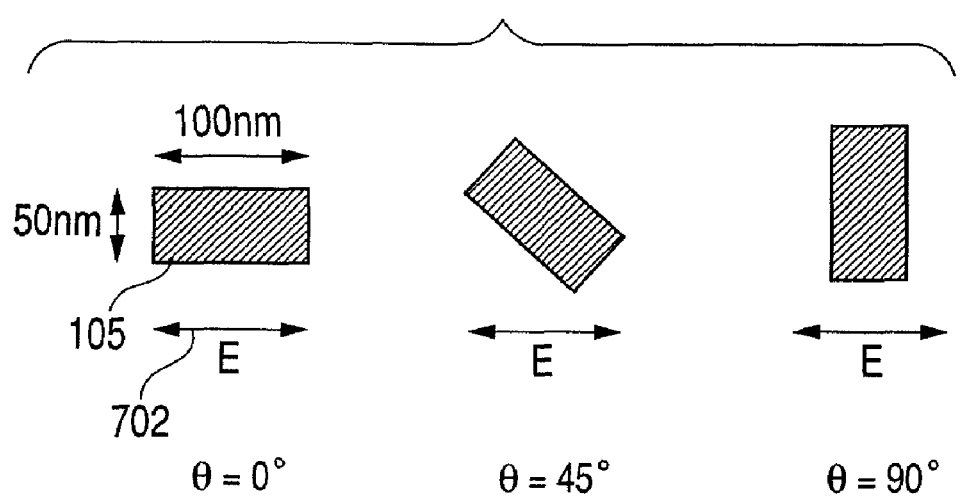

FIGS. 14A and 14B are explanatory drawings for describing a standard data which is stored in a memory device of a data processing section (A) 501, according to the present example. FIG. 14A is a graph formed by using one part of data of a dependency of absorbance of the target substance-detecting apparatus on polarizing angle, and curves 141, 142, 143, 144 and 145 are plots of which the angles of incidence are 0 degree, about 5 degrees, about 40 degrees, about 45 degrees and about 90 degrees, respectively. FIG. 14B is a schematic view for describing the angle θ of incidence. Here, the standard data stored in the memory device is a standard data in a state in which a specified amount of an anti-IgE antibody is immobilized on the target substance-detecting element, which will be described later.

FIG. 14B illustrates a relationship between each of target substance-detecting elements 105 having the angles θ of incidence respectively set at 0 degree, 45 degrees and 90 degrees and a direction 702 indicating a direction of an electric field vector of incident light. At this time, the direction 702 is parallel to a vibration direction of the incident light.

A method of detecting the target substance of the present example will now be described below.

Firstly, the target substance-detecting element is attached to a reaction well 1301 as illustrated in FIGS. 4A and 4B. Then, the anti-IgE antibody is immobilized on the target substance-detecting element.

Then, the target substance-detecting apparatus measures an absorbance spectrum of the target substance-detecting element on which the anti-IgE antibody is immobilized, as having been described in Embodiment 2. The angle of incidence is adjusted in an operation procedure as illustrated in FIG. 9 by using values of absorbance in the respective peaks of a first absorbance spectrum and a second absorbance spectrum and the above described standard data.

After the adjustment for the angle of incidence has been finished, a buffer solution which has been adjusted to the optimal pH value for detecting the IgE antigen is injected into the reaction well 1301 to clean the reaction well 1301 and the target substance-detecting element.

Subsequently, 100 μL of a specimen solution containing the IgE antigen is injected into the reaction well 1301 with a micropipetter. Then, an antigen-antibody reaction occurs in the reaction well 1301.

When two hours have passed after the antigen-antibody reaction had started, the specimen solution is extracted with a micropipetter, and an IgE antigen which is non-specifically absorbed by the antibody is washed away by the buffer solution.

After the IgE antigen has been washed, the buffer solution is injected again, and the absorbance of the target substance-detecting element on which the antigen-antibody reaction has been performed is measured. Then, an absorbance spectrum corresponding to the first absorbance regarding polarization of the target substance-detecting element in each target substance sensor can be obtained, as is illustrated in FIG. 12C.

A relationship between the concentration of the IgE antigen and a shifted amount of a peak wavelength in the present example is shown in a graph as illustrated in FIG. 13B, which is similar to Example 1.

In the present example, an optimum angle of incidence for detecting the target substance is calculated in the target substance-detecting apparatus. Therefore, the number of rotation times of the target substance-detecting element in the present example is more likely to be reduced than that of the target substance-detecting apparatus described in the Example 1. Since the angle of incidence can be adjusted quickly, the target substance can be detected with high accuracy and at a high speed.

Example 3

In the present example, a target substance-detecting apparatus illustrated in FIG. 10 described in Embodiment 3 is used for detecting a target substance.

A memory of a data processing section (B) 1002 stores a standard data similar to the standard data stored in a data processing section (A) 501 described in Example 2. When the standard data are graphed, the graphs are as illustrated in FIG. 14A, for instance.

In the present example, CRP (C-reactive protein) is used as the target substance.

A method for detecting the target substance according to the present example will now be described below.

Firstly, the target substance-detecting element is attached to a reaction well 1301 as illustrated in FIGS. 4A and 4B. Then, an anti-CRP antibody is immobilized on the target substance-detecting element.

Subsequently, the target substance-detecting apparatus measures an absorbance spectrum of the target substance-detecting element on which the anti-CRP antibody is immobilized, as having been described in Embodiment 3. Then, a correction factor (C) is determined in an operation procedure as illustrated in FIG. 11.

After the correction factor C is determined, a buffer solution which has been adjusted to the optimal pH value for detecting a CRP antigen is injected into a reaction well 1301 to clean the reaction well 1301 and the target substance-detecting element.

Subsequently, 100 μL of specimen solution containing the CRP antigen is injected into the reaction well 1301 with a micropipetter. Then, an antigen-antibody reaction occurs in the reaction well 1301.

When the specimen solution is injected, the absorbance spectrum is measured each time a predetermined time elapses. At this time, a correction value defined by Expression (2) is calculated for the first absorbance which is actually measured whenever the absorbance spectrum is measured.

When two hours has passed after the antigen-antibody reaction had started, the specimen solution is extracted with a micropipetter, and the CRP antigen which is non-specifically absorbed by the antibody is washed away by the buffer solution.

Figure 15A:
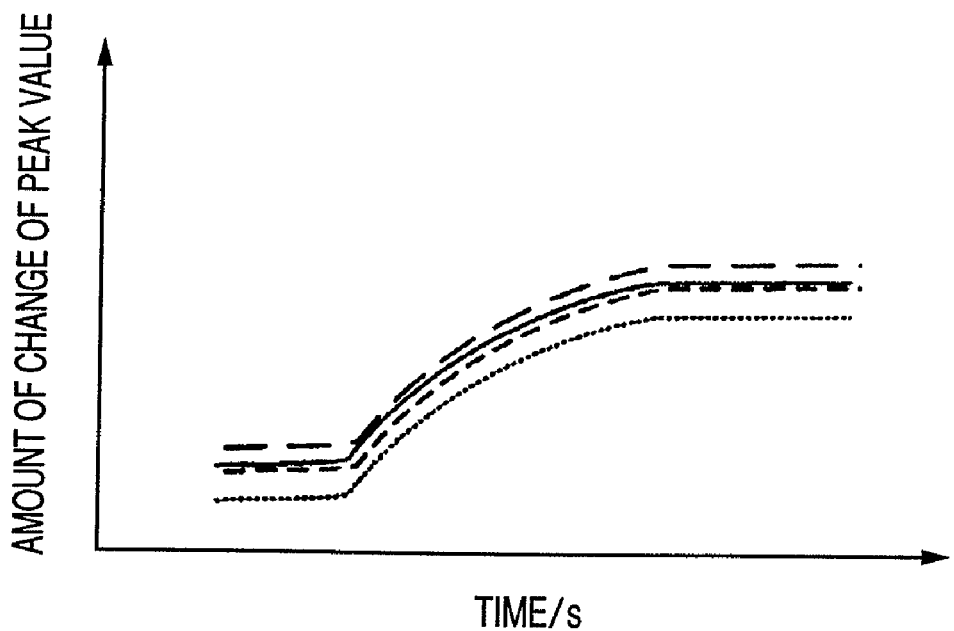
FIGS. 15A and 15B are explanatory drawings for describing Example 3.
Figure 15B:
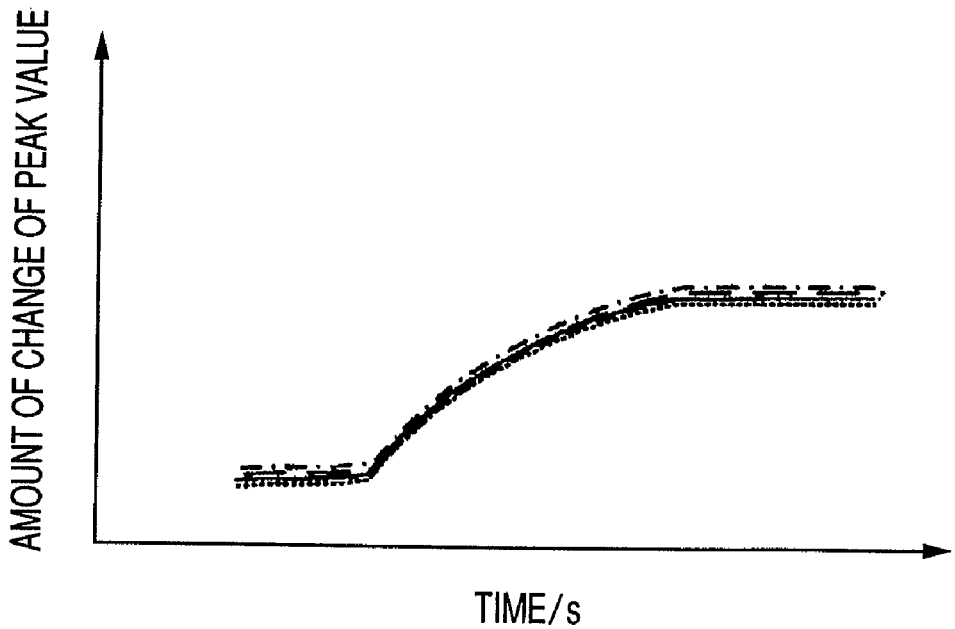

The absorbance spectrum (not shown) of each time is analyzed with a peak fitting technique, for instance, by using a software. As a result, graphs as are illustrated in FIGS. 15A AND 15B are obtained in which a horizontal axis is set as time and a vertical axis is set as a shifted amount of a peak-absorption. Reaction time characteristics between the target substance and a capturing body with time can be confirmed according to FIGS. 15A and 15B.

FIG. 15A illustrates a graph obtained when the data has not been corrected with a method as described in Embodiment 3, and FIG. 15B illustrates a graph obtained when the data has been corrected. When comparing FIG. 15A with 15B, it can be confirmed that a variation of a shifted amount with respect to a particular length of time is reduced by correcting the data. Thereby, the target substance can be detected with high accuracy.

In the example, the correction factor is determined by using the standard data stored in a memory prior to an operation of detecting the target substance; and when the target substance is detected, the measured absorbance is corrected with the use of the determined correction factor. Thereby, the corrected absorbance shows an equivalent result to the absorbance measured when the angle of incidence was optimal for detecting the target substance.

According to the present example, the target substance can be detected with high accuracy without adjusting the angle of incidence with a rotation mechanism.

While the present invention has been described with reference to examples, it is to be understood that the invention is not limited to the disclosed examples. The scope of the following claims is to be accorded the broadest interpretation so as to encompass all such modifications and equivalent structures and functions.

This application claims the benefit of Japanese Patent Application No. 2007-163712, filed Jun. 21, 2007, which is hereby incorporated by reference herein in its entirety.

What is claimed is:

1. A target substance-detecting apparatus comprising:
   a target substance-detecting element comprising metal structures;
   a light irradiation section for irradiating the target substance-detecting element with a light;
   a light-polarizing section which polarizes the irradiating light and separates an output light emitted from the target substance-detecting element into a first polarized light and a second polarized light having a vibration direction different from that of the first polarized light;
   a first light-receiving section for outputting a first signal according to intensity of the first polarized light;
   a second light-receiving section for outputting a second signal according to intensity of the second polarized light; and
   a control section which determines a peak of absorbance of the first polarized light by measuring the absorbance from the first signal, determines a peak of absorbance of the second polarized light by measuring the absorbance of the second polarized light from the second signal, and controls the target substance-detecting element so that the peak value of the first absorbance is maximized and simultaneously the peak value of the second absorbance is minimized by controlling an incidence angle of formed by a vibration direction of the incident light and a main axis of the target substance-detecting element.

2. The target substance-detecting apparatus according to claim 1, further comprising
   a data processing section having a memory device, wherein the memory device has standard data of the first absorbance based on the intensity of the first polarized light and the second absorbance based on the intensity of the second polarized light, according to each of the angles of incidence of lights.

3. The target substance-detecting apparatus according to claim 1, wherein
   the control section has a rotation mechanism which varies the peak values of the first absorbance and the second absorbance by rotating the target substance-detecting element, and
   determines an angle to which the rotation mechanism rotates the target substance-detecting apparatus, based on a plurality of the standard data stored in the memory device.

4. The target substance-detecting apparatus according to claim 1, wherein
   the control section has a rotation mechanism which varies the peak values of the first absorbance and the second absorbance by rotating the vibration direction of the incident light, and
   determines an angle to which the rotation mechanism rotates the target substance-detecting apparatus, based on a plurality of the standard data stored in the memory device.

5. A method for detecting a target substance comprising the steps of:
   irradiating a target substance-detecting element comprising metal structures with the polarized light;
   separating a light emitted from the target substance-detecting element into a first polarized light and a second polarized light having a vibration direction different from that of the first polarized light;
   determining a peak of first absorbance by measuring the first absorbance based on intensity of the first polarized light; determining a peak of second absorbance by measuring the second absorbance based on intensity of the second polarized light;
   maximizing the peak value of the first absorbance and simultaneously minimizing the peak value of the second absorbance based on each of the peak values by controlling an incident angle formed by a vibration direction of the incident light and a main axis of the target substance-detecting element; and
   detecting the target substance.

6. The method for detecting the target substance according to claim 5, wherein
   the method of maximizing the peak value of the first absorbance and simultaneously minimizing the peak value of the second absorbance based on each of the peak values is a method of determining an angle of incidence, which maximizes the peak value of the first absorbance and simultaneously minimizes the peak value of the second absorbance and rotating the target substance-detecting element so as to form the angle of incidence.

7. The method for detecting the target substance according to claim 5, wherein
   the method of maximizing the peak value of the first absorbance and simultaneously minimizing the peak value of the second absorbance based on each of the peak values is a method of determining an angle of incidence, which maximizes the peak value of the first absorbance and simultaneously minimizes the peak value of the second absorbance and rotating the vibration direction of the incident light so as to form the angle of incidence.

8. The method for detecting the target substance according to claim 5, wherein the method of maximizing the peak value of the first absorbance and simultaneously minimizing the peak value of the second absorbance based on each of the peak values is a method of:

comparing the peak value of the first absorbance and the peak value of the second absorbance with standard data including the first absorbance based on the intensity of the first polarized light and the second absorbance based on the intensity of the second polarized light, according to each of the angles of incidence of the light incident on the target substance-detecting element, which have been previously obtained;

determining an angle of incidence of the light; and rotating the target substance-detecting element or the vibration direction of the incident light.

9. The method for detecting the target substance according to claim 5, wherein the method of maximizing the peak value of the first absorbance and simultaneously minimizing the peak value of the second absorbance based on each of the peak values is a method of:

comparing the peak value of the first absorbance and the peak value of the second absorbance with standard data including the first absorbance based on the intensity of the first polarized light and the second absorbance based on the intensity of the second polarized light, according to each of the angles of incidence of the light, which have been previously obtained;

calculating a correction factor C from the peak value of the first absorbance for a light with the angle of incidence in the standard data and the maximum peak value of the first absorbance in the standard data; and correcting a measured value with the use of the correction factor C.

* * * * *